(12) United States Patent
Schülein et al.

(10) Patent No.: US 7,169,289 B2
(45) Date of Patent: Jan. 30, 2007

(54) ELECTROCHEMICAL DETECTION METHOD AND DEVICE

(75) Inventors: Jürgen Schülein, Spardorf (DE); Björn Grassl, Nürnberg (DE); Jörg Hassmann, Erlangen (DE)

(73) Assignee: November Aktiengesellschaft Gesellschaft für Molekulare Medizin, Erlagen (DE)

( * ) Notice: Subject to any disclaimer, the term of this patent is extended or adjusted under 35 U.S.C. 154(b) by 0 days.

(21) Appl. No.: 10/517,436

(22) Filed: Feb. 10, 2005

(65) Prior Publication Data
US 2005/0211571 A1 Sep. 29, 2005

(30) Foreign Application Priority Data
Jun. 28, 2002 (DE) ................ 102 29 210
Jun. 29, 2002 (DE) ................ 102 29 374

(51) Int. Cl.
*G01N 27/327* (2006.01)

(52) U.S. Cl. ................ 205/777.5; 204/403.01

(58) Field of Classification Search ........... 204/411, 204/412, 406, 403.01, 403.14; 205/777.5, 205/778
See application file for complete search history.

(56) References Cited

U.S. PATENT DOCUMENTS

| | | |
|---|---|---|
| 4,315,753 A | 2/1982 | Bruckenstein et al. |
| 4,488,556 A * | 12/1984 | Ho ................ 600/348 |
| 4,655,880 A | 4/1987 | Liu |
| 5,149,629 A | 9/1992 | Rishpon et al. |
| 5,217,112 A | 6/1993 | Almon |
| 5,260,663 A * | 11/1993 | Blades .............. 324/442 |
| 5,830,343 A | 11/1998 | Hintsche et al. ........ 205/775 |
| 6,818,109 B2 * | 11/2004 | Hashimoto et al. .... 204/403.04 |
| 2001/0029048 A1 | 10/2001 | Ding et al. |
| 2003/0022150 A1* | 1/2003 | Sampson et al. ......... 435/4 |

FOREIGN PATENT DOCUMENTS

DE 41 36 779 A1 5/1993
DE 100 15 818 A1 10/2001

* cited by examiner

*Primary Examiner*—Alex Noguerola
(74) *Attorney, Agent, or Firm*—Manabu Kanesaka

(57) ABSTRACT

A device for the electrochemical detection of at least one biochemical molecule contained in a liquid from a group of predetermined biochemical molecules includes a holder (1) for taking up the liquid, with at least one reference electrode (RE) and at least one counterelectrode (GE) and a multiplicity of working electrodes (AE1, AE2, AE3). At least one working electrode is provided for the detection of each biochemical molecule, and is coated with a molecule that is complementary to the respective biochemical molecule, so that the biochemical molecules can be detected simultaneously. The device includes a potentiostat (P) for generating a predetermined voltage profile between the working electrodes and the reference electrode, a current/voltage converter (S1, S2, S3) connected downstream of each of the working electrodes for holding all of the working electrodes at the same potential, and a measurement device (Ad) for measuring the currents flowing through the working electrodes.

12 Claims, 1 Drawing Sheet

ELECTROCHEMICAL DETECTION METHOD AND DEVICE

Figure 1:
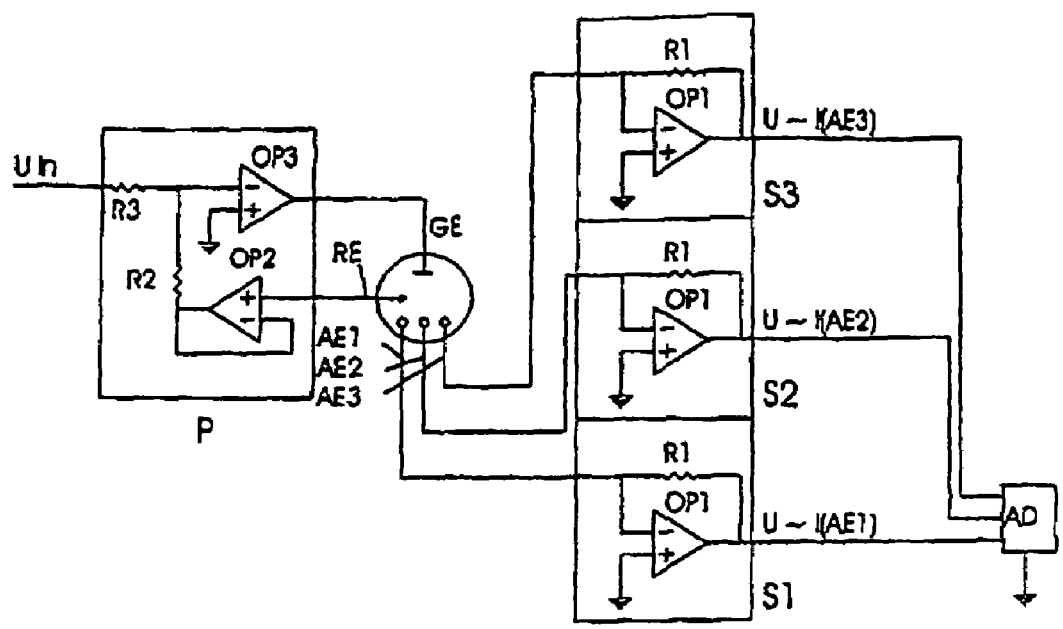

The invention relates to a device and a method for the electrochemical detection of at least one biochemical molecule—contained in a liquid—from a group of predetermined biochemical molecules. The invention relates in particular to a device for the detection of pathogens in a body fluid, e.g. blood.

For the measurement of electrochemical potentials, potentiostats having two or more working electrodes are used according to the prior art. Potentiostats having a plurality of working electrodes are also referred to as multipotentiostats. Such multipotentiostats have a reference electrode, a counterelectrode and a plurality of working electrodes. The voltage between a working electrode and the reference electrode is regulated by means of the voltage present between the counterelectrode and the respective working electrode.

A predetermined voltage profile between each of the working electrodes and the reference electrode is generated separately for each working electrode.

U.S. Pat. No. 5,830,343 discloses a method in which the voltage dropped across a multiplicity of working electrodes can be measured simultaneously by means of a multipotentiostat. In this case, a particular predetermined potential with respect to the reference electrode is applied to each working electrode independently of the others. Consequently, potentials form during the measurement between the working electrodes. This makes the evaluation of the currents measured at the rest of the working electrodes complicated.

U.S. Pat. No. 5,149,629 discloses a method for the electrochemical detection of molecules contained in a solution, in which measurement is effected sequentially by means of a plurality of working electrodes. The implementation of such a measurement is time-consuming.

U.S. Pat. No. 4,315,753 describes a method and a device for simultaneously determining the concentration of second oxygen-containing gases. The device has a potentiostat with two current followers that are connected to one another in order to generate a differential signal. The known device does not make it possible to specifically detect a plurality of biochemical molecules contained in a solution.

U.S. Pat. No. 4,655,880 discloses a device for the detection of glucose. This uses two working electrodes, one of which is coated with the glucose oxidase enzyme. The other working electrode is uncoated and serves for background measurement. A simultaneous measurement of different biochemical molecules is not possible with the known device.

Paeschke, Manfred et al.: Voltammetric Multichannel Measurements Using Silicon Fabricated Microelectrode Arrays; in: Electroanalysis 1996, 8, No. 10; pages 891 to 898, describe a voltammetric method using a multichannel potentiostat. The multichannel potentiostat described is complicated to produce. Apart from that, in practice stability problems often result during the measurement. A specific detection of biochemical molecules contained in a solution is thus possible only to a limited extent.

DE 41 36 779 A1 describes a device for the simultaneous detection of various gas components. The device comprises various working electrodes, a common counterelectrode and also a common reference electrode. The potential of each working electrode can be regulated separately by means of the device. The corresponding regulating circuit is complicated and susceptible to disturbance.

DE 100 15 818 A1 discloses a biosensor. In order to detect an analyte contained in a solution, the oxidation and reduction potential of said analyte is measured at a respective electrode. Two electrodes per analyte to be detected are thus necessary. The biosensor proposed is relatively complicated to produce. A simultaneous detection of a plurality of biochemical molecules contained in a liquid is thereby not possible.

It is an object of the invention to eliminate the disadvantages according to the prior art. The intention is to specify in particular a device and a method which enable a simultaneous electrochemical detection of different biochemical modules contained in a liquid to be carried out simply, cost-effectively and rapidly. According to a further aim of the invention, the intention is to be able to obtain measurement results that are as accurate as possible.

This object is achieved by means of the features of claims 1 and 12. Expedient refinements emerge from the features of claims 2 to 11, 13 and 14.

The invention provides a device for the electrochemical detection of a biochemical molecule—contained in a liquid—from a group of predetermined biochemical molecules, having a means for taking up the liquid, said means having at least one reference electrode and at least one counterelectrode and also a multiplicity of working electrodes, at least one working electrode (AE1, AE2, AE3) being provided for the detection of each biochemical molecule, said working electrode being coated with a molecule that is complementary to the respective biochemical molecule, so that the biochemical molecules can be detected simultaneously, a potentiostat for generating a predetermined voltage profile between the working electrodes and the reference electrode, a current/voltage converter being connected downstream of each of the working electrodes, the current/voltage converters holding all of the working electrodes at the same potential and a means for measuring the currents flowing through the working electrodes.

The device proposed is constructed in a simple manner. It enables a rapid detection of at least one biochemical molecule contained in a body fluid, e.g. of a pathogen. The device can be adapted to the biochemical molecules to be detected in a simple manner through the choice of a suitable coating of the working electrode. The type and the number of the biochemical molecules contained in the "group" is given by the number of working electrodes coated with different complementary biochemical molecules. The device also enables a simultaneous electrochemical detection of a plurality of different biochemical molecules contained in the liquid. The simultaneous detection of different biochemical molecules to be detected requires merely a single potentiostat. An identical predetermined voltage profile is thereby applied simultaneously to all of the working electrodes. By virtue of the fact that all of the working electrodes are held at the same potential, it is possible for the currents flowing through the working electrodes to be measured in parallel. For this purpose, each of the working electrodes may be connected virtually to the circuit ground via a current follower for individual evaluation of the signals. For the specific detection of the biochemical molecules contained in the liquid, the working electrodes are coated with biochemical molecules that are complementary to the biochemical molecule to be detected. The working electrodes are specific to the biochemical molecules to be detected. At least one specific working electrode is provided for each biochemical molecule to be detected. The complementary biochemical molecules bind specifically to the biochemical molecules to be detected. The electrochemical signal of the working electrode changes owing to the formation of a compound formed from the biochemical molecule to be detected and the complementary biochemical molecule.

In the sense of the present invention, a "multiplicity of working electrodes" is understood to mean more than two working electrodes.

According to one advantageous refinement, a plurality of interconnected or capacitively coupled reference electrodes are provided. The measurement speed can thereby be further increased. In this connection, it is also possible for a plurality of interconnected counterelectrodes to be provided.

The measuring means expediently has an analog-to-digital converter. Furthermore, a multiplexer may be provided, so that a virtually contemporaneous or simultaneous measurement of the currents flowing through the working electrodes is possible.

According to a further refinement, the current/voltage converter is a current follower having a first operational amplifier, a noninverting input of the operational amplifier being grounded and the inverting input thereof being connected via a first resistor to the output of the first operational amplifier and to the working electrode. A capacitance may be connected in parallel with the first resistor. This makes it possible, in a simple manner, to suppress noise and thus to increase the sensitivity.

It is possible for first resistors of different magnitudes to be connected in between the inverting input and the output of the first operational amplifier for the purpose of setting the current measurement range. This makes it possible to vary the current measurement range in a simple manner. The current measurement range can be set individually for each working electrode to the optimum range for the biochemical molecule to be detected. The device is universally suitable for the detection of a wide variety of biochemical molecules.

The biochemical molecule to be detected may be a nucleic acid and the complementary biochemical molecule may be nucleic acids that are complementary to the nucleic acid to be detected. In the case of a hybridization of such nucleic acids, there is a change in the current profile through the corresponding working electrode. Such a change indicates that the solution contains a nucleic acid that is complementary to the nucleic acid bound to the working electrode. Such a detection is highly sensitive and extremely specific. The biochemical molecules may also be synthetic single-stranded nucleic acids or their natural and/or synthetic analogs, antigens, proteins, such as antibodies, antibody fragments, derivatives of antibodies or antibody fragments, nucleic acid-binding proteins, receptors or ligands.

In a further refinement, the potentiostat has a second operational amplifier, which is connected as a voltage follower and to whose noninverting input the reference electrode is connected. The potentiostat may furthermore have a third operational amplifier, to whose output the counterelectrode is connected and whose inverting input is connected via a second resistor to the output of the second operational amplifier and is connected via a third resistor to a device for generating a selectable desired voltage, and the noninverting input of the third operational amplifier being grounded. Furthermore, a capacitance may be connected in between the output of the third operational amplifier and the inverting input thereof. This stabilizes the regulation.

The invention further provides a method for the electrochemical detection of at least one biochemical molecule—contained in a liquid—from a group of predetermined biochemical molecules, having the following steps of:

a) providing a means for taking up the liquid, the means having at least one counterelectrode and a reference electrode and also a multiplicity of working electrodes, at least one working electrode (AE1, AE2, AE3) being provided for the detection of each biochemical molecule, said working electrode being coated with a molecule that is complementary to the respective biochemical molecule, so that the biochemical molecules can be detected simultaneously, b) bringing the liquid into contact with the working, counter- and reference electrodes, c) simultaneously applying a predetermined voltage profile between the working electrodes and the reference electrode, and d) measuring the currents flowing through the working electrodes, all of the working electrodes being held at the same potential during the measurement.

The measurement is effected virtually contemporaneously or simultaneously. It is expediently carried out in parallel or by means of multiplexing. In this case, the voltage present between the working electrodes and the reference electrode may be regulated with a potentiostat. The method proposed can be carried out in a relatively simple manner. It is universal and also enables the simultaneous detection of a multiplicity of different biochemical molucules in a liquid.

In the sense of the present invention, a "multiplicity of working electrodes" is understood to mean more than two working electrodes.

The predetermined voltage profile may be a voltage profile that is variable during the measurement. The voltage profile may be predetermined by means of a programmable voltage source.

The electrodes may be produced from conventional materials, for example suitable metals such as gold, silver, platinum or the like. However, it is also possible to produce the electrodes from carbon, in particular graphite. The electrodes are coated in a conventional manner, for example by the formation of covalent bonds in the case of nucleic acids. Reference is made to M I Pividori et al. (2000) *Electrochemical genosensor design: Immobilisation of oligonucleotides onto transducer surfaces and detection methods. Biosensors and Bioelectronics* 15, 291–303.

Figure 2:
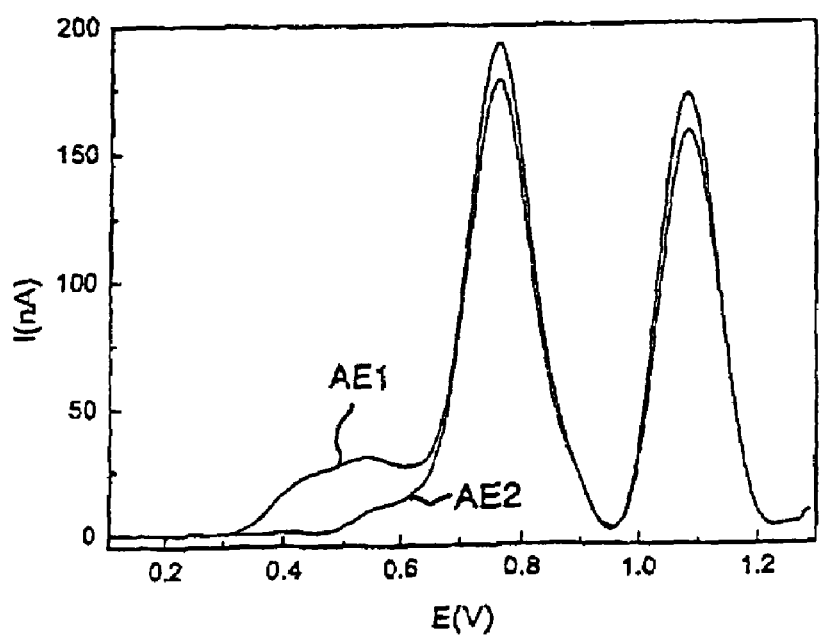

An exemplary embodiment of the invention is explained in more detail with reference to the drawing, in which:

FIG. 1 shows a schematic circuit diagram, and FIG. 2 shows a measurement result obtained with the circuit in accordance with FIG. 1.

A means for taking up the liquid containing the biochemical molecules to be detected may be e.g. a container 1 or a zone on an area produced from an insulating material, e.g. on a chip. The container 1 has working electrodes AE1, AE2, AE3, a counterelectrode GE and also a reference electrode RE. The electrodes are produced e.g. from silver, gold, platinum or graphite. The working electrodes AE1, AE2, AE3 are coated with molecules that are complementary to the biochemical molecules to be detected. Each of the working electrodes AE1, AE2, AE3 is connected to a measuring device AD via a current/voltage converter S1, S2, S3.

The current/voltage converters S1, S2, S3 in each case have an operational amplifier OP1, whose noninverting input (OP1+) is connected to circuit ground. Consequently, all of the working electrodes AE1, AE2, AE3 are held at the same potential. The inverting input OP1− of the first operational amplifier OP1 is connected to the working electrode AE1, AE2, AE3 and via a first resistor R1 to the output, which is in turn connected to the measurement device AD. For noise suppression, a capacitance (not shown here) may be connected in parallel with the first resistor R1. First resistors R1 of different magnitudes may be provided, which can be connected in an alternative manner. Thus, the measurement range can be changed in a simple manner.

The reference symbol P designates a potentiostat whose input is connected to a programmable voltage source (not shown here). The potentiostat P comprises a second operational amplifier OP2 connected as a voltage follower and a third operational amplifier OP3. The noninverting input OP2+ of the second operational amplifier OP2 is connected to the reference electrode RE. The inverting input OP2– of the second operational amplifier OP2 is connected to the output thereof and via a second resistor to the inverting input OP3– of the third operational amplifier OP3. The noninverting input OP3+ of the third operational amplifier is connected to circuit ground. The programmable circuit source (not shown here) is connected via a third resistor R3 to the inverting input OP3– of the third operational amplifier OP3 and also to the second resistor OP2. The output of the third operational amplifier OP3 is connected to the counterelectrode GE. A further capacitance (not shown here) may be connected in between the output of the third operational amplifier OP3 and the inverting input thereof.

The measuring device AD may be an analog-to-digital converter with a multiplexer. This enables a virtually contemporaneous measurement of the currents flowing through the working electrodes AE1, AE2, AE3.

By virtue of the fact that the reference electrode RE is connected to the noninverting input OP2+ of the second operational amplifier OP2, a voltage follower with a very high input impedance is obtained. An electrolysis current flowing through the reference electrode RE is thus effectively prevented. Consequently, a particularly accurate measurement is achieved.

The output of the third operational amplifier OP3 connected to the counterelectrode GE is driven during operation such that no voltage is present between the inputs OP3–, OP3+ of said operational amplifier. The noninverting input OP3+ of the third operational amplifier OP3 is connected to circuit ground. Consequently, the inverting input OP3– is also virtually grounded and thus at the same potential as the working electrodes AE1, AE2, AE3. Given suitable regulation, the current flowing through the third resistor R3 is equal to the current flowing through the second resistor R2. Since the magnitude of the voltage across the second resistor R2 is equal to that of the voltage between the reference electrode RE and the working electrodes AE1, AE2, AE3, it is possible to prescribe the potential of the working electrodes AE1, AE2, AE3 relative to the reference electrode RE by means of a proportional voltage at the input U of the potentiostat P. In practice, the second resistor R2 is expediently chosen to be equal to the third resistor R3, as a result of which the proportionality constant is fixed at the value –1. As an alternative, in this case of an additive potentiostat P, the third resistor R3 may be replaced by a plurality of resistors, thereby obtaining a plurality of inputs, e.g. for modulation.

According to one variation at the circuit, it is possible to restrict the frequency response of the current/voltage converters S1, S2, S3. As a result, the overall noise can be reduced. Such a restriction in the frequency response may be achieved by capacitors that are in each case connected in parallel with the first resistor R1. In order to enlarge the current measurement range, it may be advantageous to embody the first resistors R1, if appropriate with capacitors connected in parallel therewith, in switchable fashion by means of relays or analog electronic switches or a combination of the two.

FIG. 2 shows the result of measurements carried out with the circuit according to the invention. For this purpose, uncoated working electrodes were brought into contact with a DNA-containing solution. The measurement was effected by means of differential pulse voltammetry. The current difference measured at the working electrode in each case before and after a voltage modulation is plotted against the voltage in FIG. 2. The left-hand peak shows the oxidation of guanine of DNA adsorbed at the working electrode. The right-hand peak shows the oxidation of adenine. The results plotted are those which were obtained by measurement at a first working electrode AE1 and at a second working electrode AE2.

The present measurement exhibits only a non-specific detection of DNA in a solution. Given a suitable coating of the working electrodes, it is possible within the scope of the invention to detect specifically predetermined DNA or the like in a solution. The number of DNA sequences or the like to be detected specifically depends on the number of working electrodes used.

LIST OF REFERENCE SYMBOLS

1 Container
OP1, 2, 3 first, second, third operational amplifier
P Potentiostat
S1, 2, 3 first, second, third current/voltage converter
R1, 2, 3 first, second, third resistor
AD Measuring device
AE1, 2, 3 Working electrodes
GE Counterelectrode
RE Reference electrode
U Output of a programmable voltage source

The invention claimed is:

1. A device for the electrochemical detection of at least one type of a biochemical molecule contained in a liquid from a group of predetermined biochemical molecules of different types, comprising:

a means (1) for taking up the liquid, said means having at least one reference electrode (RE) and at least one counterelectrode (GE) and more than two working electrodes (AE1, AE2, AE3), with at least one working electrode (AE1, AE2, AE3) being provided for the detection of each type of a biochemical molecule, said working electrode being coated with a molecule that is complementary to the biochemical molecule to be detected, so that biochemical molecules of different types can be detected simultaneously, a current/voltage converter (S1, S2, S3) being connected downstream of each of the working electrodes (AE1, AE2, AE3) and having a first operational amplifier (OP1) and a first resistor (R1), the current/voltage converters (S1, S2, S3) holding all of the working electrodes (AE1, AE2, AE3) at the same potential, a means (AD) for measuring the currents flowing through the working electrodes (AE1, AE2, AE3), and a potentiostat (P) for generating a predetermined voltage profile which is variable during the measurement between the working electrodes (AE1, AE2, AE3) and the reference electrode (RE), said potentiostat (P) comprising a second operational amplifier (OP2) and a second resistor (R2), and a third operational amplifier (OP3) and a third resistor (R3), with the third operational amplifier (OP3), to whose output the counterelectrode (GE) is connected and whose inverting input (0P3−) is connected via the second resistor (R2) to the output of the second operational amplifier (OP2), being connected via the third resistor (R3) to a device for generating a selectable desired voltage, with the noninverting input (0P3+) of the third operational amplifier (OP3) being grounded.

2. The device as claimed in claim 1, wherein a plurality of interconnected or capacitively coupled reference electrodes (RE) is provided.

3. The device as claimed in claim 1, wherein a plurality of interconnected counterelectrodes (GE) is provided.

4. The device as claimed in claim 1, wherein the measuring means has an analog-to-digital converter.

5. The device as claimed in claim 1, wherein the current/voltage converter (S1, S2, S3) is a current follower having a the first operational amplifier (OP1), a noninverting input (OP1+) of the first operational amplifier (OP1) is grounded, and the inverting input (OP1−) thereof is connected via the first resistor (R1) to the output of the first operational amplifier (OP1) and to the working electrode (AE1).

6. The device as claimed in claim 5, wherein a capacitance is connected in parallel with the first resistor (R1).

7. The device as claimed in claim 5, wherein first resistors (R1) of different magnitudes can be connected between the inverting input (OP1−) and the output of the first operational amplifier (OP1) for the purpose of setting the current measurement range.

8. The device as claimed in claim 1, wherein the biochemical molecule to be detected is a nucleic acid and the complementary biochemical molecules are nucleic acids that are complementary to the nucleic acid to be detected.

9. The device as claimed in claim 1, wherein the potentiostat (P) has a second operational amplifier (OP2), which is connected as a voltage follower and to whose noninverting input (OP2−) the reference electrode (RE) is connected.

10. The device as claimed in claim 1, wherein a capacitance is connected between the output of the third operational amplifier (OP3) and the inverting input (OP3−) thereof.

11. A method for electrochemical detection of at least one type of a biochemical molecule contained in a liquid from a group of predetermined biochemical molecules of different types, comprising the steps of:

a) providing a means (1) for taking up the liquid, the means (1) having at least one counterelectrode (GE) and a reference electrode (RE) and more than two working electrodes (AE1, AE2, AE3), with at least one working electrode (AE1, AE2, AE3) being provided for the detection of each biochemical molecule, said working electrode being coated with a molecule that is complementary to the biochemical molecule to be detected, so that biochemical molecules of different types can be detected simultaneously, b) bringing the liquid into contact with the working (AE1, AE2, AE3), counter- (GE) and reference electrodes (RE), c) simultaneously applying a predetermined voltage profile which is variable during the measurement between the working electrodes (AE1, AE2, AE3) and the reference electrode (RE), while regulating said voltage between the working electrodes (AE1, AE2, AE3) and the reference electrode (RE) with a potentiostat (P) for generating a predetermined voltage profile which is variable during the measurement between the working electrodes (AE1, AE2, AE3) and the reference electrode (RE), said potentiostat (P) comprising a second operational amplifier (OP2) and a second resistor (R2), and a third operational amplifier (OP3) and a third resistor (R3), with the third operational amplifier (OP3), to whose output the counterelectrode (GE) is connected and whose inverting input (OP3−) is connected via the second resistor (R2) to the output of the second operational amplifier (OP2), being connected via the third resistor (R3) to a device for generating a selectable desired voltage, with the noninverting input (OP3+) of the third operational amplifier (OP3) being grounded, and d) measuring the currents flowing through the working electrodes (AE1, AE2, AE3), all of the working electrodes (AE1, AE2, AE3) being held at the same potential during the measurement.

12. The method as claimed in claim 11, wherein the measurement is carried out in parallel or by means of multiplexing.

* * * * *